United States Patent [19]

Mori

[11] Patent Number: 4,763,971
[45] Date of Patent: Aug. 16, 1988

[54] SOLAR RAYS RADIATION DEVICE FOR MEDICAL TREATMENT

[76] Inventor: Kei Mori, 3-16-3-501, Kaminoge, Setagaya-ku, Tokyo, Japan

[21] Appl. No.: 931,460

[22] Filed: Nov. 14, 1986

[30] Foreign Application Priority Data

Dec. 10, 1985 [JP] Japan .................. 60-277768

[51] Int. Cl.4 .................. G02B 6/00; G02B 6/04
[52] U.S. Cl. .................. 350/96.1; 350/96.24
[58] Field of Search ............ 350/96.10, 96.15, 96.24

[56] References Cited

U.S. PATENT DOCUMENTS 4,297,000 10/1981 Fries .................. 350/96.1 X
4,511,755 4/1985 Mori .................. 350/96.10 X
4,653,472 3/1987 Mori .................. 350/96.10 X

FOREIGN PATENT DOCUMENTS 0015339 2/1977 Japan .................. 350/96.1

Primary Examiner—Eugene R. LaRoche
Assistant Examiner—Nathan W. McCutcheon
Attorney, Agent, or Firm—Jordan and Hamburg

[57] ABSTRACT

A solar rays radiation device for medical treatment includes an automatic solar rays collecting and transmitting device on an automobile. Solar rays collected by the automatic solar rays collecting and transmitting device are transmitted through an optical conductor cable into the automobile and emitted from the end portion of the optical conductor cable to treat a person in the automobile.

4 Claims, 3 Drawing Sheets

SOLAR RAYS RADIATION DEVICE FOR MEDICAL TREATMENT

BACKGROUND OF THE INVENTION

The present invention relates to a solar rays radiation device for medical treatment, in particular, a solar rays radiation device for medical treatment in which an automatic solar rays collecting and transmitting device is mounted on an automobile such as a car, solar rays collected by the automatic solar rays collecting and transmitting device are guided through an optical conductor cable in the automobile, and medical treatment is performed by radiating the solar rays onto a diseased part of or other desired parts of a patient in the automobile.

In the recent years, a large number of persons suffer from incurable diseases such as arthritis, neuralgia and rheumatism, or from pain of an injury, a bone fracture, or an ill-defined disease. Furthermore, a person cannot avoid aging or one's skin which progresses gradually from a comparatively young age. On the other hand, the present applicant has previously proposed to focus solar rays or artificial light rays by use of lenses or the like, to guide the same into an optical conductor, and to transmit those rays onto an optional desired place through the optical conductor. These solar rays or artificial light rays transmitted in such a way are employed for use in illuminating or for other like purposes, for example, to cultivate plants, chlorella, or the like. In the process thereof, visible light rays not containing ultraviolet, infrared, etc. promote a living body reaction, and thereby the same promote health of a person or prevent the person's skin from showing signs of aging. Furthermore, the visible light rays have noticeable effects in treating a patient for arthritis, neuralgia, bedsore, rheumatism, injuries, bone fractures, or the like and stopping the pain of those diseases. Such effects obtained by use of the device according to the present invention have been already found by the present applicant.

And further, in consideration of the actual situation as mentioned above, the present applicant has previously proposed a light rays radiation device for medical treatment capable of performing various medical treatments or beauty treatment or promotion of a person's health by radiating the light rays corresponding to the visible light rays component of solar rays not containing harmful components such as ultraviolet, infrared, etc.

A light rays radiation device for medical treatment which has been previously proposed by the present applicant comprises an optical conductor cable and cylindrical hood member. Solar rays or artificial light rays are guided into the optical conductor cable from an end portion thereof, and the guided light rays are transmitted therethrough. Light rays (white-colored light rays) corresponding to the visible light rays component of solar rays are transmitted through the optical conductor cable in such a manner as proposed previously by the present applicant in various ways. The cylindrical hood member is installed at the light rays emitting end portion of the optical conductor cable. At the time of medical treatment, a patient sits in a chair and the light rays of the visible light rays component transmitted through an optical conductor cable in such a manner as mentioned before are radiated onto the diseased part of the patient.

As mentioned above, the light rays radiated onto the diseased part of the patient are the light rays corresponding to the visible light rays component of solar rays containing therein neither ultraviolet nor infrared. Thereby, medical treatment can be done without suffering from any deleterious effects due to ultraviolet and infrared.

The time period for performing medical treatment by solar rays radiation as mentioned above is about 20 to 30 minutes per one time. Such time period is considered to be sufficient for medical treatment. By repeating radiation of solar rays everday as mentioned above, the effect of medical treatment can be heightened raised or the health of a person can be promoted. However, the persons living in these modern days are very busy, and thereby they have limited time to take the trouble to go to a place full of equipment for performing such medical treatment.

SUMMARY OF THE INVENTION

A primary object of the present invention is to provide a solar rays radiation device for medical treatment including an automatic solar rays collecting and transmitting device mounted on an automobile.

It is another object of the present invention to provide a solar rays radiation device which is utilized for bathing with solar rays in an automobile on the way to and from a place of work, during movement from one place to the other by driving an automobile, or during the time of parking at a place full of sun shine.

It is another object of the present invention to provide an automobile carrying thereon an automatic solar rays collecting and transmitting device and transferring it to a place full of sun shine for taking solar rays radiation therein.

The above-mentioned features and other advantages of the present invention will be apparent from the following detailed description which goes with the accompanying drawings.

DESCRIPTION OF THE PREFERRED EMBODIMENTS

Figure 1:
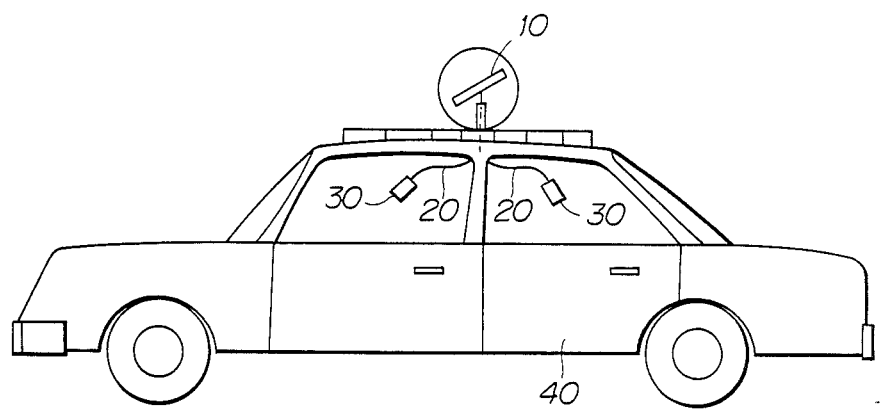
FIG. 1 is an elevational view for explaining an embodiment of the present invention.

FIG. 1 is an elevation view for explaining an embodiment of a solar rays radiation device for medical treatment according to the present invention. In FIG. 1, 10 is an automatic solar rays collecting and transmitting device, 20 is an optical conductor cable, 30 is a cylindrical hood member and 40 is an automobile.

In the present invention, the automatic solar rays collecting and transmitting device 10 is mounted on the automobile 40 as shown in FIG. 1. The solar rays collected by the automatic solar rays collecting and transmitting device 10 are guided into the optical conductor cable 20 and are transmitted into the automobile 40 through the optical conductor cable 20. Thereby, a patient can receive medical treatment by solar rays radiation in the automobile 40.

Moreover, in the case of the embodiment shown in FIG. 1, the automatic solar rays collecting and transmitting device 10 is mounted on the automobile 40 by use of a supplementary instrument. Therefore, the automobile 40 does not need any improvement. Furthermore, it is not necessary to set always the automatic solar rays collecting and transmitting device 10 on the automobile 40.

During the time of transferring, the device 10 is put in the automobile and it can be employed on the condition of setting it on the automobile or on the neighboring desired place only at the time that it is to be used. And further, the afore-mentioned automatic solar rays collecting and transmitting device 10 requires a power supply for controlling a solar rays focusing lens so as to direct it to the sun. The battery on the automobile may be used as the power supply. Otherwise, a solar battery is mounted on the roof of the automobile or at a place in the automatic solar rays collecting and transmitting device 10, for employing it as the power supply.

Figure 2:
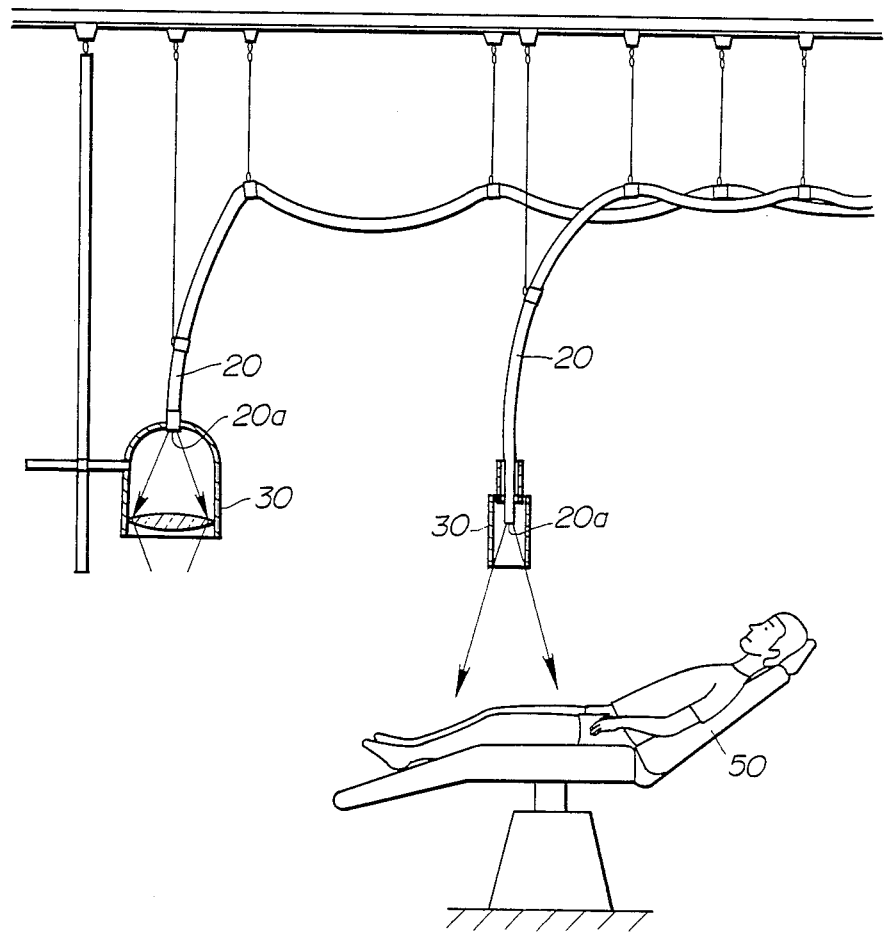
FIG. 2 is an elevational view for showing an embodiment of a solar rays radiation device for medical treatment which has been previously proposed by the present applicant.

FIG. 2 is a construction view for explaining an embodiment of a solar rays radiation device for medical treatment which has been previously proposed by the present applicant. In FIG. 2, 20 is an optical conductor cable having an end portion not shown in FIG. 2 for guiding solar rays therefrom, and the guided solar rays are transmitted through the optical conductor cable 20. Light rays (white-colored light rays) corresponding to the visible light rays component of solar rays are transmitted through the optical conductor cable 20 in such a manner as proposed previously by the present applicant in various ways.

In FIG. 2, 30 is a cylindrical hood member installed at a light rays emitting end portion 20a of the above-mentioned optical conductor cable 20, and 50 is a medical treatment chair. When performing medical treatment or health promotion treatment, a patient lies on the medical treatment chair 50 and the visible light rays component of the solar rays transmitted through the optical conductor cable 20 as mentioned before are radiated onto the diseased part or the other optional desired part of the patient. As mentioned heretofore, the light rays to be radiated onto the diseased part or the like of the patient are the light rays corresponding to the visible light rays component of the solar rays, which contain neither ultraviolet nor infrared. Consequently, it will be possible to perform medical treatment without suffering from any harmful influence of ultraviolet or infrared rays.

Figure 3:
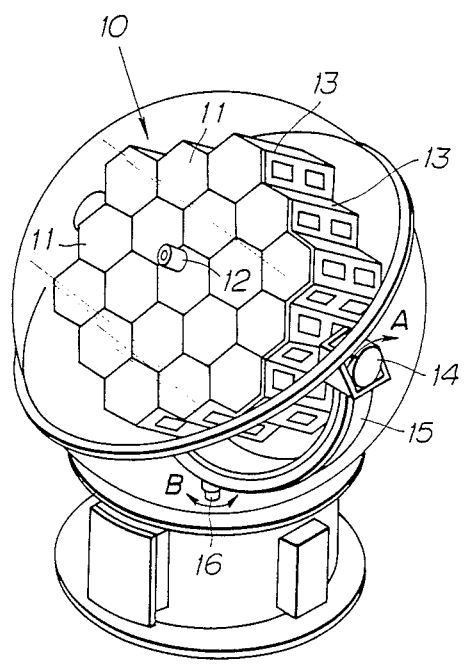
FIG. 3 is a perspective view for explaining an embodiment of a solar ray collecting device which is employed for bringing the present invention into operation.

FIG. 3 is a detailed structural view for explaining a solar ray collecting device 10 which is accommodated in a transparent dome-shaped capsule. The solar ray collecting device 10 comprises a large number of lenses 11 (nineteen lenses in the embodiment shown in FIG. 3), a solar rays direction sensor 12 for detecting the direction of the solar rays, a support frame 13 for unitarily sustaining the lenses 11 and the solar rays direction sensor 12, a first motor 14 for rotatably moving in a direction shown by arrow A the unitarily combined lenses 11, sensor 12, and support frame 13, a support part 15 for supporting the afore-mentioned lenses 11, sensor 12, support frame 13, and motor 14, a rotatable shaft 16 installed so as to meet at a right angle with the rotatable shaft of the afore-mentioned motor 14, and a second motor not shown in FIG. 3 for rotating the rotatable shaft 16 in a direction shown by arrow B.

The direction of the solar rays is detected by the afore-mentioned solar rays direction sensor 12. The signal generated by the sensor 12 controls the first motor and the second motor so as to direct the lenses 11 toward the sun at al times. The solar rays focused by the lenses 11 are guided into the optical conductor cable 20, the light receiving end portion of which is located at the focus position of the lenses 11. And further, the solar rays are transmitted through the optical conductor cable into the automobile 40 as shown in FIG. 1.

As is apparent from the foregoing description, according to the present invention, the meritorius effects of solar rays utilization can be obtained in combination with an automobile as mentioned below.

In the case of mounting the device on the private car, the solar rays can be radiated onto the human body of a person staying in the car during inactive spare time going to and from work or going from home by driving a car for the purpose of performing medical treatment or promoting the health of the person.

And further, in the case of setting the device on the automobile specially employed for medical treatment, the automobile is hired to go to a desired place and at a desired time, both of which are previously designated, and transferred to a place full of sun shine. Utilizing the necessary minimum period of time, a person staying in the automobile can receive medical treatment by solar rays radiation. Furthermore, even a patient with advanced disease or serious illness who cannot attend a hospital can receive medical treatment in the automobile ordered to go to a desired place.

I claim:

1. A solar rays radiation device for effecting medical treatment of a person in a motor vehicle in which the motor vehicle has a motor vehicle body formed in part by a motor vehicle roof, comprising solar rays collecting means mounted on the top of said motor vehicle roof, said collecting means comprising a plurality of lenses, motor operated means mounted on said collecting means for moving said collecting means about two mutually perpendicular axes, a solar rays direction sensor mounted on said collecting means for detecting the direction of the solar rays and for controlling said motor operated means such that said motor operated means moves said collecting means about said two axes to continuously direct said lenses toward the sun, whereby said lenses continuously receive the direct rays of the sun as the motor vehicle travels about on land and as the position of the sun changes relative to earth as the time of day passes, said collecting means being operable to transmit solar rays corresponding to the visible light rays component of solar rays and excluding ultraviolet rays and infrared rays, an optical conductor cable means leading from said collecting means to the inside of said motor vehicle body and receiving said visible light rays component of solar rays from which ultraviolet rays and infrared rays have been excluded, said optical conductor means having a light emitting end portion, and a hood means in said motor vehicle body on which said light emitting end portion is mounted such that the visible light rays component emitted from said light emitting end portion pass through said hood means to be directed to a desired portion on a person who is riding inside of said motor vehicle body.

2. A solar rays radiation device according to claim 1 wherein said motor vehicle has a battery, said motor operated means being operated by said battery.

3. A solar rays radiation device according to claim 1 wherein said collecting means comprises separation means for separating out ultraviolet rays and infrared rays from the solar rays and for transmitting only the visible light to said optical conductor means.

4. The combination comprising a motor vehicle and a solar rays radiation device for effecting medical treatment of a person riding in said motor vehicle, the combination comprising:

a motor vehicle having a motor vehicle body with a roof; and a solar rays collection means mounted on the top of said roof, said collecting means comprising a plurality of lenses, motor operated means mounted on said collection means for moving said collection means about two mutually perpendicular axes, a solar rays direction sensor mounted on said collection means for detecting the direction of the solar rays and for controlling said motor operated means such that said motor operated means moves said collecting means about said two axes to continuously direct said lenses toward the sun, whereby said lenses continuously receive the direct rays of the sun as the motor vehicle travels about on land and as the position of the sun changes relative to earth as the time of day passes, said collecting means being operable to transmit solar rays coresponding to the visible light rays component of solar rays and excluding ultraviolet rays and infrared rays, an optical conductor cable means leading from said collecting means to the inside of said motor vehicle body and receiving said visible light rays component of solar rays in which ultraviolet rays and infrared rays have been excluded, said optical conductor means having a light emitting end portion, and a hood means within said motor vehicle body on which said light emitting end portion is mounted such that the visible light rays component emitted from said light emitting end portion pass through said hood means to be directed to a desired portion on a person who is riding inside of said motor vehicle body.

* * * * *